(12) United States Patent
Duncan

(10) Patent No.: US 9,301,754 B2
(45) Date of Patent: Apr. 5, 2016

(54) MEDICAL DEVICE FOR PORT CLOSURE

(71) Applicant: Cook Medical Technologies LLC, Bloomington, IN (US)

(72) Inventor: Kate Duncan, Mooresville, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 285 days.

(21) Appl. No.: 14/132,673

(22) Filed: Dec. 18, 2013

(65) Prior Publication Data

US 2014/0180336 A1    Jun. 26, 2014

Related U.S. Application Data

(66) Substitute for application No. 61/739,993, filed on Dec. 20, 2012.

(51) Int. Cl.
*A61B 17/068* (2006.01)
*A61B 17/064* (2006.01)
*A61B 17/00* (2006.01)

(52) U.S. Cl.
CPC ......... *A61B 17/0644* (2013.01); *A61B 17/0057* (2013.01); *A61B 17/064* (2013.01); *A61B 17/068* (2013.01); *A61B 17/0684* (2013.01); *A61B 2017/0061* (2013.01); *A61B 2017/00623* (2013.01); *A61B 2017/00659* (2013.01); *A61B 2017/00668* (2013.01)

(58) Field of Classification Search
CPC ........... A61B 17/0644; A61B 17/0057; A61B 17/0684; A61B 17/068; A61B 17/10
See application file for complete search history.

(56) References Cited

U.S. PATENT DOCUMENTS

| 3,869,957 | A |   | 3/1975  | Barth et al. |
|-----------|---|---|---------|--------------|
| 4,407,286 | A |   | 10/1983 | Noiles et al. |
| 5,119,983 | A | * | 6/1992  | Green et al. ............... 227/179.1 |
| 5,242,457 | A | * | 9/1993  | Akopov et al. ............... 606/144 |
| 5,766,189 | A |   | 6/1998  | Matsuno |
| 6,464,710 | B1|   | 10/2002 | Foster |
| 6,652,545 | B2|   | 11/2003 | Shipp et al. |

* cited by examiner

*Primary Examiner* — Victor Nguyen
(74) *Attorney, Agent, or Firm* — Brinks Gilson & Lione

(57) ABSTRACT

The present invention provides devices for safely closing an opening in tissue. In one embodiment, the medical device includes a delivery tube, a control member and a staple. The delivery tube is elongated and extends from a proximal end to a distal end to define a longitudinal axis. The delivery tube defines a tube lumen, while the control member is elongated and extends through the tube lumen. The staple is releasably attached to the control member adjacent the distal end of the delivery tube. The staple formed of a resilient material having a C-shape, the C-shape including free ends defining first and second tines. The resilient material of the staple is elastically deformable such that the staple may flex to change a distance between the first and second tines. The free ends are spaced apart a first distance in an unbiased state of the staple.

20 Claims, 5 Drawing Sheets

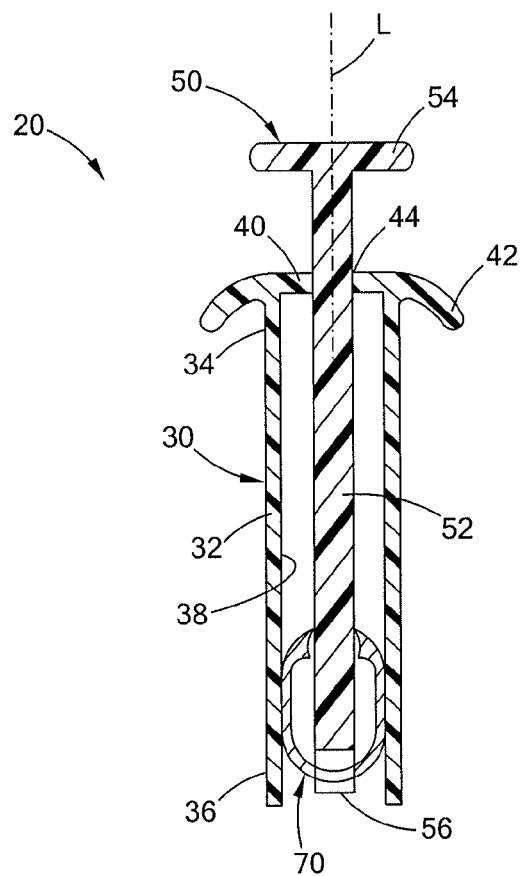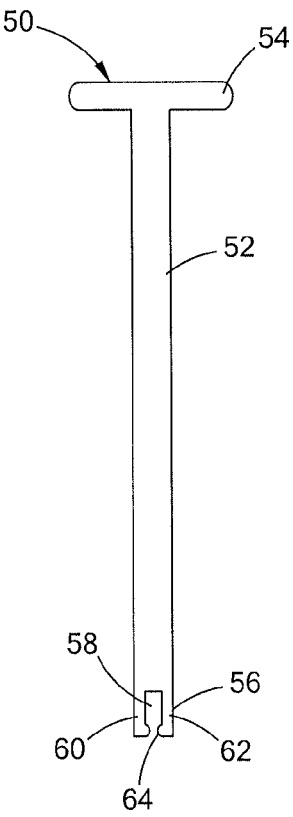
FIG. 1   FIG. 2
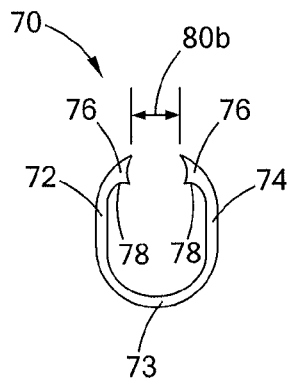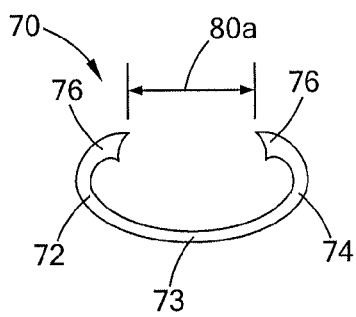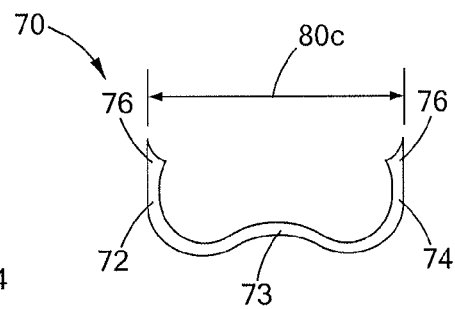
FIG. 3   FIG. 4   FIG. 5

MEDICAL DEVICE FOR PORT CLOSURE

CROSS-REFERENCE TO RELATED APPLICATIONS

This application claims the benefit of U.S. Provisional Application Ser. No. 61/739,993 filed on Dec. 20, 2012, entitled "MEDICAL DEVICE FOR PORT CLOSURE" the entire contents of which are incorporated herein by reference.

FIELD OF THE INVENTION

The present invention relates generally to suturing percutaneous openings, such as openings used to access an internal organ, body cavity or bodily lumen, such as in laparoscopy or gastropexy.

BACKGROUND OF THE INVENTION

Among the most significant advances in medical surgical techniques has been the adoption, and now-routine performance, of a variety of minimally invasive procedures. These minimally invasive procedures are distinguishable from conventional open surgical procedures in that access to a body cavity of a patient is achieved through a relatively small incision through the tissue, such as the skin and underlying fascia layers. A tubular medical device (or tubular portion of a device) may be inserted or introduced through the incision into the body cavity for carrying out a medical procedure. Laparoscopy is one such procedure and is commonly used to treat a variety of internal bodily structures. Many other types of external percutaneous connections also provide a patient or medical staff with access to an internal organ or bodily lumen. For example, semi-permanent connections are made through the skin for placement of IV lines, catheters, dialysis lines, colostomy bags in the like. Percutaneous endoscopic gastrostomy tubes, commonly known as PEG tubes, are used as a means of feeding when a person is unable to eat. Gastropexy is a procedure to suture the stomach to the skin around and access site, e.g. for longer term placement of such connection tubes.

The puncture at the access site is typically closed by suturing, or by manually providing pressure on the site until clotting and/or wound sealing occurs. Suturing is more often utilized for larger punctures, whereas manual pressure is more often utilized in connection with smaller punctures. The manual method, however, can take half an hour or more, and requires the patient to remain substantially immobilized for at least that period of time while pressure is applied by medical personnel to the access site. In addition, it may be necessary for the patient to remain in the hospital for a period of time thereafter for observation. Furthermore, there may be a possibility of clot formation at the puncture site.

Utilizing sutures to close the opening may have procedure variability, which may require additional time to close the vessel. When sutures are utilized to close a larger vascular access site, they typically are of the "purse-string" type. In this type of suture, a single thread is stitched to surround the access site, and then pulled tight (like a purse-string) to close the access site. Performing this suture typically requires a good deal of skill and practice on the part of the physician. It also may be difficult to perform this type of suturing in a key-hole type procedure, or in other types of surgery where there is limited access to the wound site. Damage to the underlying body structures is also a concern when suturing such openings, as is the proper suturing of the fascia layers beneath the skin.

BRIEF SUMMARY OF THE INVENTION

The present invention provides medical devices for safely closing an opening in tissue without using sutures or needles, thus making the procedure quicker and easier to perform while reducing the risk of damaging underlying body structures. In one embodiment, the medical device includes a delivery tube, a control member and a staple. The delivery tube is elongated and extends from a proximal end to a distal end to define a longitudinal axis. The delivery tube defines a tube lumen, while the control member is elongated and extends through the tube lumen. The staple is releasably attached to the control member adjacent the distal end of the delivery tube. The staple formed of a resilient material having a C-shape, the C-shape including free ends defining first and second tines structured to pierce the tissue and an intermediate body connecting the first and second tines. The resilient material of the staple is elastically deformable such that the staple may flex to change a distance between the first and second tines. The free ends are spaced apart a first distance in an unbiased state of the staple.

The medical device generally includes three configurations, namely a first deployed configuration, a second delivery configuration, and a third insertion configuration. In the first deployed configuration the staple is located outside of the tube lumen in its unbiased state. In the second delivery configuration the staple is positioned within the tube lumen in a compressed state where the free ends have been moved towards each other. In the third insertion configuration the staple is located outside of the tube lumen in an expanded state where the free ends have been moved away from each other.

According to more detailed aspects, the free ends are spaced apart a third distance in the third insertion configuration, the third distance being greater than a smallest inner diameter of the delivery tube. In the third insertion configuration, the staple is pressed against the distal end of the delivery tube to flex the staple. For example, a proximal force on the control member causes the staple to be pressed against the distal end. In the second delivery configuration, the free ends are spaced apart a second distance that is less than the first distance. In the third insertion configuration, the free ends are spaced apart a third distance that is greater than the first distance.

According to further detailed aspects, the staple is attached to the control member such that the first and second tines of the staple extend away from the intermediate member in a proximal direction for retrograde insertion of the staple into the tissue. The staple is preferably formed of a resorbable or degradable material. In one configuration, the distal end of the delivery tube includes a distal end surface that is angled less than 90 degrees relative to the longitudinal axis and structured to engage the first and second tines in the first deployed configuration. In another configuration, the tube lumen has an oblong cross-sectional shape such that it is elongated in a direction transverse to the longitudinal axis. The delivery tube may also have an oblong cross-sectional shape such that it is elongated in a direction transverse to the longitudinal axis and defines a minor outer diameter that is less than a major outer diameter, the first distance between the free ends of the staple tines being greater than the minor outer diameter. In these configurations, the oblong shape defines major and minor axes, wherein the staple extends in a staple plane generally aligned with the major axis in the second delivery configuration, and generally aligned with the minor axis in the third insertion configuration.

According to still further detailed aspects, the control member is attached only to the intermediate member of the staple. The control member preferably includes an adjustable slot sized to receive the staple. Generally, the control member includes first and second grasping fingers moveable relative to each other and structured to grasp the staple therebetween. In one configuration, the control member is formed of a resilient material that flexes to adjust the size of the slot. In another configuration, the grasping fingers are longitudinally slidably relative to each other. In yet another configuration, the grasping fingers are pivotally attached for relative rotation therebetween.

According to even further detailed aspects, the first and second tines and intermediate member of the staple are each curved to form the C-shape. Preferably, the first and second tines extend primarily radially inwardly towards the longitudinal axis in the unbiased state, and extend primarily longitudinally away from the intermediate member in the expanded state. The first and second tines and intermediate member of the staple may be unitarily and integrally formed.

BRIEF DESCRIPTION OF THE DRAWINGS

FIG. 1 is a cross-sectional view taken from the front of a medical device constructed in accordance with the teachings of the present invention;

FIG. 2 is front view of a control member forming a portion of the medical device depicted in FIG. 1;

FIG. 3 is a front view showing the compressed state of a staple forming a portion of the medical device of FIG. 1;

FIG. 4 is a front view showing the unbiased state of the staple of FIG. 3;

FIG. 5 is a front view showing an expanded state of the staple of FIG. 3;

DETAILED DESCRIPTION OF THE INVENTION

Figure 7:
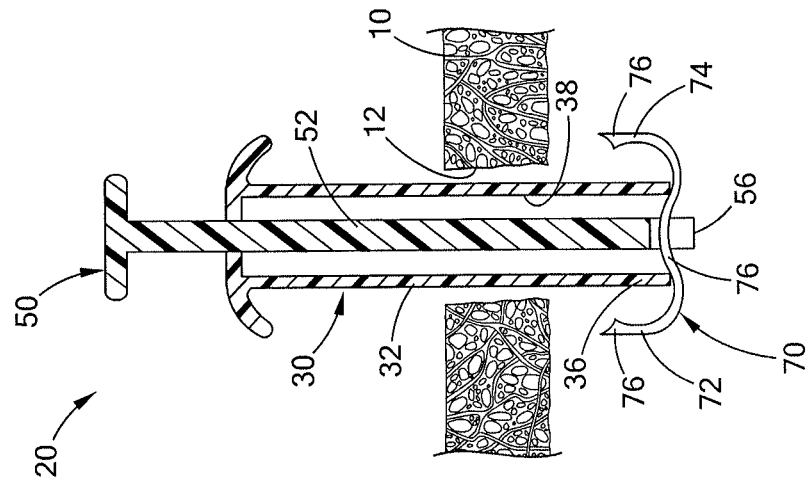
FIG. 7 is a front cross-sectional view of the medical device of FIG. 1 showing an insertion configuration.

The terms "proximal" and "distal" as used herein are intended to have a reference point relative to the user. Specifically, throughout the specification, the terms "distal" and "distally" shall denote a position, direction, or orientation that is generally away from the user and towards a target site, and the terms "proximal" and "proximally" shall denote a position, direction, or orientation that is generally towards the user and away from a target site. Thus, "proximal" and "distal" directions, portions of a device, or bodily regions, may depend on the point of entry for the procedure (e.g., percutaneously or laparoscopically or endoscopically).

Turning now to the figures, FIG. 1 depicts a medical device 20 for closing and opening 12 in tissue 10 (shown in FIG. 6) that eliminates sutures and needles and reduces the risk of damage to underlying body structures. The medical device 20 generally comprises an elongated delivery tube 30, an elongated control member 50, and a staple 70.

The delivery tube 30 is defined by a tubular wall 32 which is elongated between a proximal end 34 to a distal end 36 and defines a longitudinal axis L therebetween. The delivery tube 30, and in particular its side wall 32, define a tube lumen 38 which slidably receives the control member 50. That is, the side wall 32 is tubular, and preferably cylindrical although any tubular cross-sectional shape may be employed. The delivery tube 30 further includes a proximal end wall 40 which closes off the proximal end of the tube lumen 38. The end wall 40 projects laterally away (i.e. away the longitudinal axis L) from the side wall 32 on opposite sides thereof (if not all directions away from the tube 30) to define a handle 42. The proximal end wall 40 also includes a guide hole 44 which slidably receives the control member 50 and assists in maintaining its radial position within the tube 30.

The delivery tube 30 is preferably formed of a rigid plastic such as ABS or polycarbonate, and is preferably insert molded. The delivery tube 30 may be formed as a single piece or may be formed in two lateral halves and snapped together. Other suitable materials for forming the tube 30 include polycarbonates (PC), polyamides including Nylon™, polytetrafluorethylenes (e.g. PTFE and EPTFE), polyethylene ether keytones (PEEK), polyvinylchlorides (PVC), polyimides, polyurethanes, and polyethylenes (high, medium or low density), including multi-layer or single layer constructions with or without reinforcing elements. Metals or alloys such as stainless steel, titanium, nitinol or other metals/alloys or ceramics can be employed.

As best seen in FIG. 2, the control member 50 generally comprises an elongated rod 52 having a proximal end defining a grasping flange 54 and a distal end 56 defining an attachment means. In this embodiment, the attachment means formed at the distal end 56 of the control member 50 comprises a slot 58 extending longitudinally through a distal end surface of the rod 52. The slot 58 thus defines two grasping fingers 60, 62 which are enlarged at their distal ends to define a narrow throat 64. The throat 64 is sized to be smaller than a thickness of the staple 70, and the fingers 60, 62 flex to enlarge the throat 64 to permit a releasable attachment to the staple 70. The control member 50 is preferable molded from a plastic similar to that of the delivery tube 30, including any of those listed above, and may also be formed from metals or alloys such as stainless steel, titanium, nitinol or the like.

Turning now to FIGS. 3-5, the staple 70 generally comprises a first tine 72 connected to a second tine 74 by an intermediate body 73. Together, the first and second tines and intermediate body 72, 73, 74 give the staple 70 a C-shape. The free ends 76 of the first and second tines 72, 78 may define barbs 78 for engaging the tissue 10. The staple 70 is preferably formed of a resorbable or degradable material. The staple 70 can be die cut from Cook Biodesign™ or could be made of polyglactin or other resorbable or degradable material as is known in the art, such as polylactide (PLA), polyglycolide (PGA), poly-L-lactide (PLLA), poly-DL-lactide (PDLLA) and their copolymers (e.g., PGLA, PLGA), resorbable homopolymers, copolymers, or blends of resorbable polymers.

Specific examples of suitable resorbable materials include poly-alpha hydroxy acids such as polylactic acid, polyglycolic acid (PGA); tri-methlyene carbonate; polycaprolactone; poly-beta hydroxy acids such as polyhydroxybutyrate or polyhydroxyvalerate; or other polymers such as polyphosphazines, polyorgano-phosphazines, polyanhydrides, polyesteramides, poly-orthoesters, polyethylene oxide, polyesterethers (e.g., poly-dioxanone) or polyamino acids (e.g., poly-L-glutamic acid or poly-L-lysine). There are also a number of naturally derived resorbable polymers that may be suitable, including modified polysaccharides, such as cellulose, chitin, and dextran, and modified proteins, such as fibrin and casein and the like. As used herein, the term "resorbable" refers to the ability of a material to be absorbed into a tissue and/or body fluid upon contact with the tissue and/or body fluid.

The staple 70 is generally attached to the distal end 56 of the control member 50 by forcing the intermediate body 73 through the throat 64 and into the slot 58. Notably, the staple 70 is used to close the opening 12 in a retrograde fashion, and thus the tines 72, 74 extend proximally from the intermediate body 73 and point back towards the operator. In the depicted embodiment, this may be accomplished by distally moving the control member 50 such that its distal end 56 projects from the distal end 36 of the tube 30, thus allowing the staple 70 to be releasably attached to the control member 50. The staple 70 is then compressed, e.g. manually by the operator using fingers or a tool, and the control member 50 and staple 30 are moved together proximally relative to the delivery tube 30 such that they are located within the tube lumen 38 of the delivery tube 30 as shown in FIG. 1. Alternatively, the delivery tube 30 may exclude the proximal end wall 40 or may otherwise have an enlarged hole 44 such that the staple 70 may be first attached to the control member 50 and inserted from the proximal end 34 of the delivery tube 30.

Accordingly, FIG. 1 depicts a delivery configuration of the medical device 20 where the staple 70 is in a compressed state (biased towards a natural uncompressed state), which is also shown in FIG. 3. A natural, unbiased state of the staple 70 is shown in FIG. 4. In the unbiased state, the free end 76 of the first and second tines, 72, 74 are spaced apart a first distance 80a. In the compressed state shown in FIG. 3, the free ends 76 are spaced apart a second distance 80b that is smaller than the first distance 80a. FIG. 5 depicts an expanded state of the staple 70, wherein the free ends 76 are spaced apart a third distance 80c that is larger than the first distance 80a, and likewise larger than the second distance 80b. In the unbiased state (FIG. 4) the tines 72, 74 extend primarily radially inwardly towards the longitudinal axis, whereas they extend primarily longitudinally away from the intermediate member 76 in the expanded state (FIG. 5), as will be discussed in more detail hereinbelow.

Figure 6:
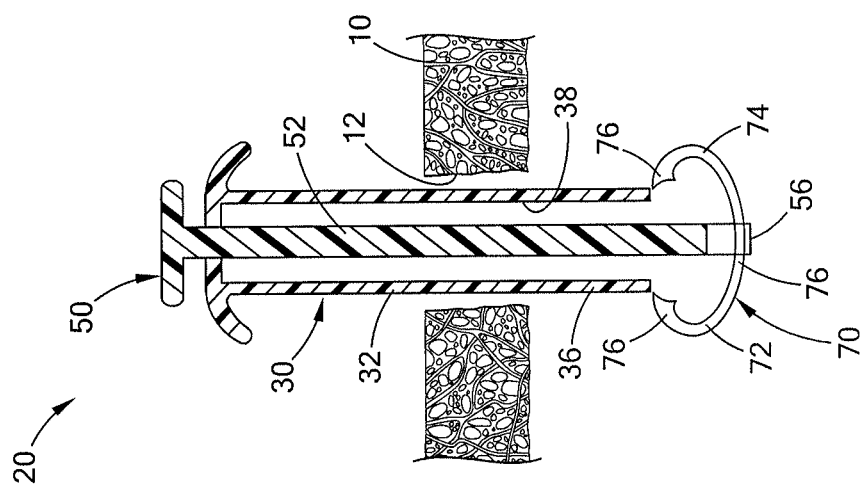
FIG. 6 is a front cross-sectional view of the medical device of FIG. 1 depicting a deployed configuration.

When the medical device 20 is placed in its second delivery configuration shown in FIG. 1, the medical device 20 may be passed through an opening 12 and tissue 10. Once the distal end 36 is placed sufficiently past the tissue 10, as shown in FIG. 6, the control member 50 may be moved distally relative to the delivery tube 30 such that the staple 70 is forced out of the distal end 36 of the tube 30. Once fully released, the staple 70 takes its unbiased state which was previously shown in FIG. 4 and also shown in FIG. 6. In the unbiased state, the distance 80a between the free ends 76 of the first and second tines 72, 74 is sized to be larger than a diameter of the tube lumen 38 (i.e., larger than an inner diameter of the tube 30). In this way, the control member 50 may then be moved back proximally relative to the delivery tube 30, thereby also moving the staple 70 proximally relative to the delivery tube 30.

Relative movement of the delivery tube 30 and control member 50 is then used to move the staple 70 into its expanded state, as shown in FIG. 7 and previously depicted in FIG. 5. Generally, a proximal force is placed on the intermediate body 73 of the staple 70 by the control member 50, while the distal end 36 of the delivery tube 30 presses against portions of the staple positioned radially outside the rod 52. These locations can be considered either a part of the intermediate body 73, a part of the first and second tines 72, 74, or the junction therebetween. While the unbiased state of the staple 70 generally has a C-shaped configuration as shown in FIG. 4, the expanded state of the staple 70 generally comprises a U-shape or W-shape such that the first and second tines 72, 74 point primarily in a proximal direction, in contrast to the radially inward direction they point in the unbiased state.

Figure 9:
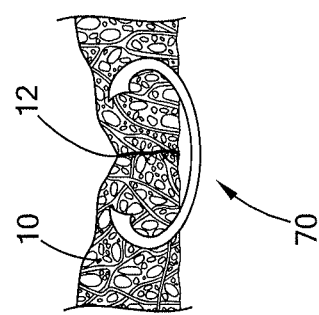
FIGS. 8 and 9 are front cross-sectional views showing operation of the medical device of FIG. 1 to close an opening in tissue.
Figure 8:
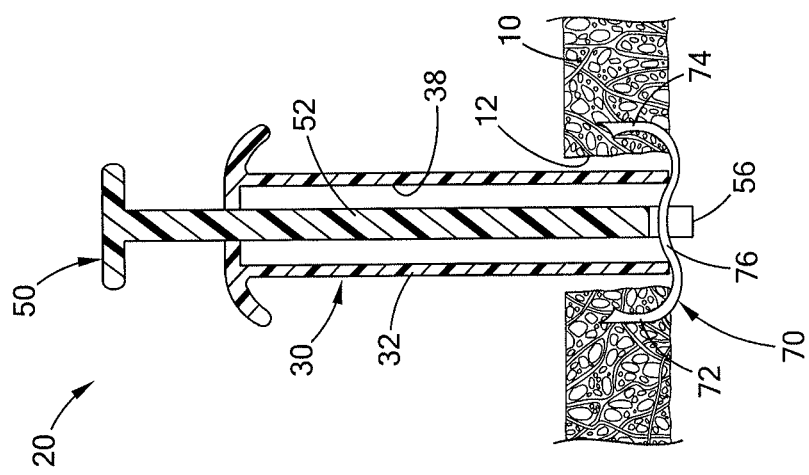

In this third insertion configuration shown in FIG. 7, the entire medical device 20 may be moved proximally relative to the tissue 10 such that the first and second tines 72, 74 extend into the tissue 10, as shown in FIG. 8. Once sufficiently positioned in the tissue 10, the delivery tube 30 and control member 50 may be moved longitudinally relative to one another to remove the forces placed on the staple 70 so that it can again resume its unbiased state (previously shown in FIG. 4 and the first deployed configuration of FIG. 6). Once deployed, the staple 70 can sufficiently approximate the tissue 10, i.e. bring the tissue at the sides of the opening 12 in sufficient proximity such they will heal, as shown in FIG. 9. During this healing process, the staple 70 will become absorbed or degrade. Various sizes of the delivery tube 30 and staple 70, to match differently sized openings 12 in the tissue 10, are preferably provided as a kit to provide a solution to closing many types of perforations.

Figure 10:
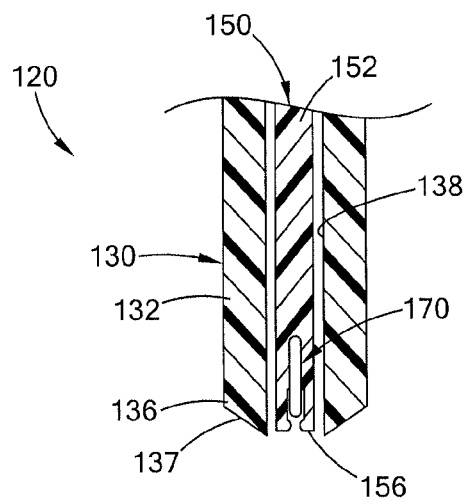
FIG. 10 is a cross-sectional view, taken from the side and partially cut away, of an alternate embodiment of the medical device of FIG. 1.
Figure 11:
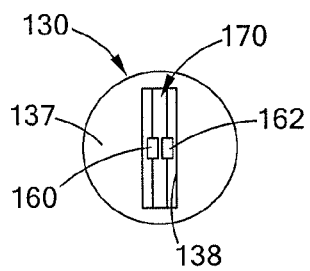
FIG. 11 is an end view of the medical device of FIG. 10.

Turning now to FIG. 10, an alternate embodiment of the medical device 120 is depicted. Similar reference numerals have been used in all alternative embodiments to shown common parts with the previous embodiment. Again the medical device 120 generally includes a delivery tube 130, a control member 150 and a staple 170. The control member 150 and elongated rod 152 are of substantially identical construction to the previous embodiment. In this embodiment, the side wall 32 of the delivery tube is much thicker and defines a tube lumen 138 that is sized to more closely receive the control member 150 and staple 170. As best seen in the end view of FIG. 11, the tube lumen 138 has an oblong cross-sectional shape, meaning it has a first minor diameter that is smaller than a second major diameter. In FIG. 11 the tube lumen 138 is shown as having a rectangular cross-section. Accordingly, this tube lumen 138 helps prevent twisting of the control staple 170 while within the delivery tube 130.

Figure 12:
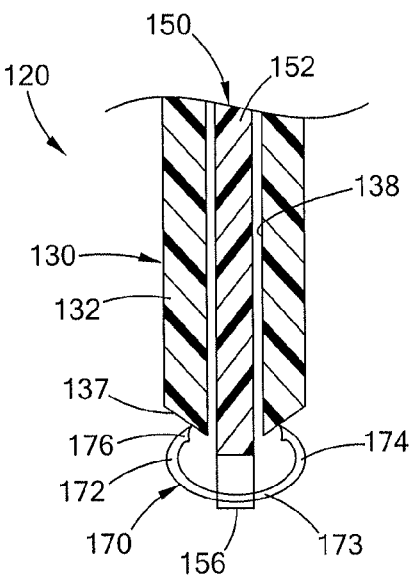
FIG. 12 is a cross-sectional view of the medical device of FIG. 10 showing the deployed configuration.
Figure 13:
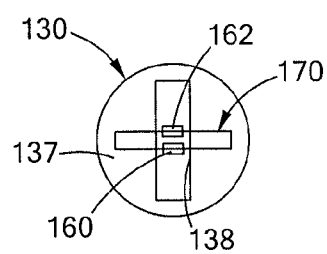
FIG. 13 is an end view of the medical device as depicted in FIG. 12.

As shown in FIGS. 10 and 12, the distal end 136 of the delivery tube 130 further defines a distal end surface 137 that is angled relative to the longitudinal axis L, and in particular less than 90 degrees. Stated another way, the distal end 136 may be chamfered, beveled, radiused (curved) or otherwise angled to promote opening of the staple 170 into its expanded state. As shown in FIGS. 12 and 13, in the deployed configuration of the medical device 120 the control member 150 may be rotated through about 90 degrees (45 degrees alone may be sufficient) such that the free ends 176 of the first and second tines 172, 174 of the staple may be pressed against the angled distal end surface 176. When the control member 150 is moved proximally relative to the delivery tube 130, the distal end surface 137 will facilitate moving the staple 170 from its unbiased state to its expanded state in the insertion configuration.

Figure 14:
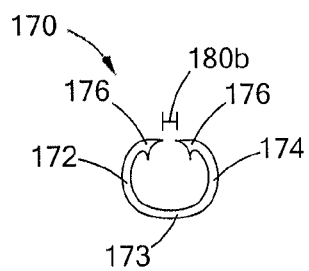
FIG. 14 is a front view showing the compressed state of a staple forming a portion of the medical device of FIG. 10.
Figure 15:
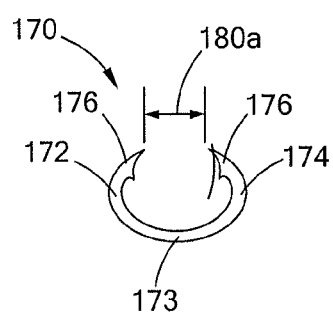
FIG. 15 is a front view showing the unbiased state of the staple of FIG. 3.
Figure 16:
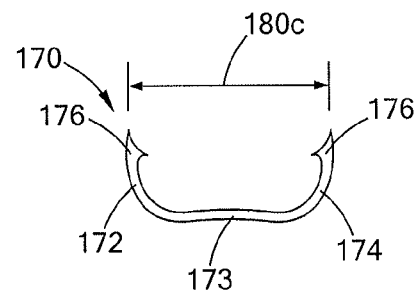
FIG. 16 is a front view showing an expanded state of the staple of FIG. 3.

Notably, and as shown in FIGS. 14 and 15, the staple 170 may be of an overall smaller size, and the first distance 180a between the free ends 176 of the tines 172, 174 does not need to be larger than an outer diameter of the delivery tube 130. As with the previous embodiment, the second distance 180b in the delivery state (FIG. 14) is smaller than the first distance 180a of the unbiased state (FIG. 15), both of which are in turn are smaller than the third distance 180c between the free ends 176 and the expanded state (FIG. 16).

Figure 17:
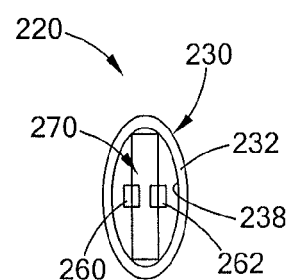
FIG. 17 is an end view another alternate embodiment of the medical device of FIG. 1.

Turning now to FIG. 17, yet another embodiment of the medical device 220 is depicted. Similar to the embodiment of FIGS. 10-16, in this embodiment the delivery tube 230 defines a tube lumen 238 which is oblong. In this embodiment, the side wall 232 of the delivery tube 230 also has an oblong cross-sectional shape. In the delivery configuration shown in FIG. 17, the staple 270 extends along the major diameter of tube lumen 238, and then can be rotated in the deployed configuration, e.g., about 90 degrees, so that the free ends of the tines are easily positioned outside of the side wall 232 of the delivery tube 230, preferably along the minor diameter of the tube lumen 238. As with the embodiment of FIGS. 10-16, this allows the first distance (for example 180a) of the staple 170, 270 to be even smaller than the embodiment of FIGS. 1-5. As such, these staples 170, 270 may more closely approximate the tissue 10 surrounding the opening 10 desired to be closed.

Figure 18:
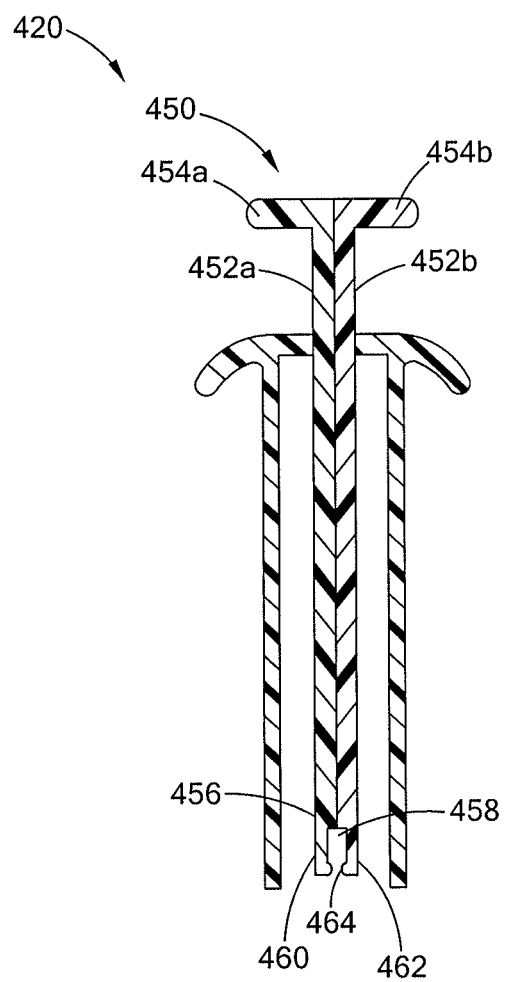
FIG. 18 is a cross-sectional view, taken from the front, of another alternate embodiment of the medical device of FIG. 1.

An additional embodiment of the medical device 420 depicted in FIG. 18. In this embodiment, the control member 450 essentially includes two rods 452a 452b which are slidable relative to one another. Each rod 452a, 452b includes a proximal end defining a grasping flange 454a, 454b. At the distal end of the control member 450, the first rod 452a defines a first finger 460 while the second rod 452b defines a second finger 462. Together, the first and second fingers 460, 462 define the slot 458 at the distal end 456 of the control member 450. In this way, the rods 452a, 452b can be slid longitudinally relative to one another to change the size of the throat 464 (essentially the longitudinal spacing of the distal ends of the rods 452a, 452b) such that the staple (not shown) can easily exit the slot 450 and become detached from the control member 450. Thus, the distal end 456 of the control member 450 defines an alternate attachment means to the previous embodiments.

Figure 19:
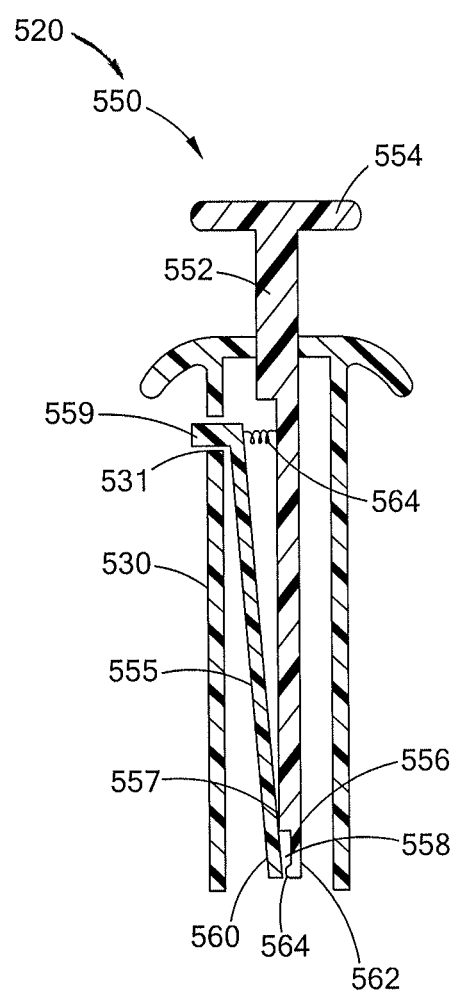
FIG. 19 is a cross-sectional view, taken from the front, of another alternate embodiment of the medical device of FIG. 1.

In still yet another embodiment of the medical device 520 depicted in FIG. 19, the control member 550 again comprises an elongated rod 552 slidably passing through the delivery tube. A proximal end of the rod 552 again defines a grasping flange 554 while the distal end 556 includes a different attachment means. In this embodiment, a pivoting rod 555 has been added and is pivotally attached to the rod 552 via a pivot point or hinge 557. A distal end of the pivoting rod 555 defines the first finger 560, while the rod 552 defines the second finger 562. Together, the first and second fingers 560, 562 define a slot 558 sized to receive the staple. The slot 558 has a narrowed throat 564 which is adjustable in size for releasable attachment of the staple.

In particular, a proximal end of the pivoting rod 555 extends radially out through a hole 531 formed near the proximal end of the delivery tube 530. The proximal end of pivoting rod 555 forms, or is attached to, a button 559 which projects outwardly from the outer surface of the delivery tube 530. A biasing member, preferably a spring 564, is positioned in between the pivoting rod 555 and the main rod 552 to bias the button 559 radially outwardly to narrow the throat 564 for holding onto the staple. Upon depressing the button 559 to move the proximal end of the pivoting rod 555 radially inwardly and compress the spring 564, the first finger 560 will be moved radially outwardly to enlarge the size of the throat 564 (and/or slot 558) and allow easy release of the staple held therein. Other mechanical variations of this attachment means will be readily envisioned by the skilled artisan, including incorporation of electro-mechanical mechanisms.

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:

1. A medical device for closing openings in tissue, the medical device comprising:
    an elongated delivery tube extending from a proximal end to a distal end and defining a longitudinal axis, the delivery tube defining a tube lumen;
    an elongated control member extending through the tube lumen of the delivery tube;
    a staple releasably attached to the control member adjacent the distal end of the delivery tube, the staple formed of a resilient material having a C-shape, the C-shape including free ends defining first and second tines structured to pierce the tissue and an intermediate body connecting the first and second tines, the resilient material of the staple being elastically deformable such that the staple may flex to change a distance between the first and second tines, the free ends spaced apart a first distance in an unbiased state of the staple; and
    the medical device having three configurations including a first deployed configuration wherein the staple is located outside of the tube lumen in its unbiased state, a second delivery configuration where the staple is positioned within the tube lumen in a compressed state where the free ends have been moved towards each other relative to the unbiased state, and a third insertion configuration wherein the staple is located outside of the tube lumen in an expanded state where the free ends have been moved away from each other relative to the unbiased state.

2. The medical device of claim 1, wherein the free ends are spaced apart a third distance in the third insertion configuration, the third distance being greater than a smallest inner diameter of the delivery tube.

3. The medical device of claim 1, wherein, in the third insertion configuration, the staple is pressed against the distal end of the delivery tube to flex the staple.

4. The medical device of claim 3, wherein a proximal force on the control member causes the staple to be pressed against the distal end.

5. The medical device of claim 1, wherein, in the second delivery configuration, the free ends are spaced apart a second distance that is less than the first distance.

6. The medical device of claim 1, wherein, in the third insertion configuration, the free ends are spaced apart a third distance that is greater than the first distance.

7. The medical device of claim 1, wherein the staple is attached to the control member such that the first and second tines of the staple extend away from the intermediate member in a proximal direction for retrograde insertion of the staple into the tissue.

8. The medical device of claim 1, wherein the distal end of the delivery tube includes a distal end surface that is angled less than 90 degrees relative to the longitudinal axis and structured to engage the first and second tines in the first deployed configuration.

9. The medical device of claim 1, wherein the tube lumen has an oblong cross-sectional shape such that it is elongated in a direction transverse to the longitudinal axis.

10. The medical device of claim 9, wherein the delivery tube has an oblong cross-sectional shape such that it is elongated in a direction transverse to the longitudinal axis and defines a minor outer diameter that is less than a major outer diameter, the first distance being greater than the minor outer diameter.

11. The medical device of claim 9, wherein the oblong cross-sectional shape defines a major axis and a minor axis, and wherein the staple extends in a staple plane generally aligned with the major axis in the second delivery configuration, and generally aligned with the minor axis in the third insertion configuration.

12. The medical device of claim 1, wherein the control member is attached only to the intermediate member.

13. The medical device of claim 1, wherein the control member includes an adjustable slot sized to receive the staple.

14. The medical device of claim 13, wherein the control member is formed of a resilient material that flexes to adjust the size of the slot.

15. The medical device of claim 1, wherein the control member includes first and second grasping fingers moveable relative to each other and structured to grasp the staple therebetween.

16. The medical device of claim 15, wherein the first and second grasping fingers are longitudinally slidably relative to each other.

17. The medical device of claim 15, the first and second grasping fingers are pivotally attached for relative rotation therebetween.

18. The medical device of claim 1, wherein the first and second tines and intermediate member each are curved to form the C-shape.

19. The medical device of claim 1, wherein the first and second tines extend primarily radially inwardly towards the longitudinal axis in the unbiased state, and extend primarily longitudinally away from the intermediate member in the expanded state.

20. The medical device of claim 1, wherein the first and second tines and intermediate member are unitarily and integrally formed.

* * * * *